United States Patent
Harrison

(10) Patent No.: US 8,501,201 B1
(45) Date of Patent: Aug. 6, 2013

(54) COMPOSITION USEFUL FOR IMPROVING SKIN

(75) Inventor: Tami Dion Harrison, Mobile, AL (US)

(73) Assignee: Tami Dion Harrison

( * ) Notice: Subject to any disclaimer, the term of this patent is extended or adjusted under 35 U.S.C. 154(b) by 0 days.

(21) Appl. No.: 13/411,558

(22) Filed: Mar. 3, 2012

(51) Int. Cl.
*A61K 9/00* (2006.01)
*A01N 43/04* (2006.01)

(52) U.S. Cl.
USPC .............................................. 424/400; 514/23

(58) Field of Classification Search
None
See application file for complete search history.

(56) References Cited

U.S. PATENT DOCUMENTS 4,304,591 A * 12/1981 Mueller et al. ................ 504/232

OTHER PUBLICATIONS

Fisher, D., et al., "How Soap Floats Your Boat", accessed on: Mar. 19, 2013, accessed from:http://candleandsoap.about.com/od/soapmakingbasics/ss/surfacetension.htm, p. 1.*

Roehm, E., et al., "Canola Oil", 2011, accessed from: http://web.archive.org/web/20111118043442/http://www.nutritionheart.com/canola-oil-health/, pp. 1-4.*

Gerardi, M.H., et al. "The Microbiology of Anaerobic Digesters", 2003, John Wiley and Sons, pp. 129.*

Diyhomespa, "Salt Foot Scrub", 2009, Diyhoespa Blog, accessed from:http://diyhomespa.wordpress.com/category/diy-home-spa-recipes/page/2/, p. 1.*

Stewart, R.E., et al., "Robin Stewart's Chemical Free-Home", 2002, Black Inc, pp. 119 and 161.*

Sally Hansen, "Sally Hansen Just Feet Deep Callus Foot Scrub", Total Beauty, 2009, accessed from: Diyhomespa and (Rastogi or LIPO VI) teach foot scrubs containing magnesium sulfate, surfactants, and propyl paraben., pp. 1-4.*

Rstogi, S.C., et al., "Contents of methyl-, ethyl,-, propyl-, butyl-, and benzylaraben in cosmetic products", 1995, Contact Dermatitis, pp. 28-30.*

LIPO VI, "Exfoliating Foot Scrub with LIPO VI 400/60", 2009, accessed from: Diyhomespa and (Rastogi or LIPO VI) teach foot scrubs containing magnesium sulfate, surfactants, and propyl paraben., pp. 1-2.*

* cited by examiner

*Primary Examiner* — Michael G Hartley
*Assistant Examiner* — Lance Rider

(57) ABSTRACT

Disclosed is a topical powder composition useful for improving rough or hard feet on the human skin comprising magnesium sulfate, vitamins, *melaleuca alternifolia*, biodegradable surfactants, sodium carbonate, water, fragrance, propylparaben, propylene glycol, may also contain one or more FD&C colors.

7 Claims, No Drawings

COMPOSITION USEFUL FOR IMPROVING SKIN

CROSS-REFERENCE TO RELATED APPLICATIONS

This non-provisional Application claims the benefit of the priority of Applicant's earlier filed U.S. Provisional Application Ser. No. 61/448,122 filed on Mar. 1, 2011, the entire contents of which are incorporated herein by reference.

BACKGROUND OF THE INVENTION

One of the major problems experienced by people is having rough feet. Many people walk daily and the shoes or sandals they wear may contribute to roughening of the feet. Previously the most common method of treatment of rough feet has been topical ointments and creams which provide minimum help and don't address the problem for people with immensely hard skin on their feet. The only solution, then, has been to wear socks and try to avoid hardening of the feet and applying ointments or creams on top of rough skin or removal of corns, calluses, or bunions by razor blade.

FIELD OF THE INVENTION

This invention describes a topical foot powder composition, useful for the prevention/treatment of rough or hard feet on human skin.

SUMMARY OF THE INVENTION

The present invention is composition useful for improving skin for prevention and treatment of rough or hard feet. A composition for skin roughening inhibiting and improving of the feet. The compositions of the present invention may be prepared by thoroughly blending all ingredients.

The composition includes about 20% to about 60% by volume magnesium sulfate. The composition may also contain vitamins. The preferred vitamins are vitamin A, and vitamin E. About 0 to about 40% by volume of at least one vitamin or combination thereof selected from group: vitamin A, vitamin C, or vitamin E, about 0% to about 20% by volume *melaleuca alternifolia*, about 40% to about 80% by volume biodegradable surfactants, about 20% to about 80% by volume sodium carbonate, about 0% to about 20% by volume water, fragrance, about 0.1% propylparaben, about 0 to about 40% propylene glycol, and the composition may also contain colors one or more colors or combination thereof selected from group: yellow5, red40, red3, blue1, or red33. The proportion of fragrance, color and oil is noncritical and thus a matter of choice.

DETAILED DESCRIPTION OF THE INVENTION

In general, the present invention provides cosmetic composition for skin roughening inhibiting and improving of the feet. The compositions of the present invention may be prepared by thoroughly mixing all ingredients.

The composition includes about 20% to about 60% by volume magnesium sulfate. The composition may also contain vitamins. The preferred vitamins are vitamin A, and vitamin E although other vitamins can be substituted and used in the compositions. about 0 to about 40% by volume of at least one vitamin or combination thereof selected from group: vitamin A, vitamin C, or vitamin E, about 0% to about 20% by volume *melaleuca alternifolia*, about 40% to about 80% by volume biodegradable surfactants, about 20% to about 80% by volume sodium carbonate, about 0% to about 20% by volume water, fragrance, about 0.1% propylparaben, about 0 to about 40% propylene glycol, and the composition may also contain colors one or more colors or combination thereof selected from group: yellow5, red40, red3, blue1, or red3, although other colors can be substituted and used in the compositions.

Generally FD&C colors are used in the invention compositions and are approved for use in food, drugs and cosmetics. D&C colors are also approved for use in drugs and cosmetics and may be used in the invention compositions. Colors can be blended to yield different shades. The INC abbreviated names for FD&C colors are as follows:

Black Color—Red 40, Blue 1, Yellow 5
Dark Blue Color—Blue 1
Sky Blue Color—Blue 1
Green Color—Yellow 5, Blue 1
Orange Color—Yellow 6
Peach Color—Yellow 5, Yellow 6
Pink Color—Red 3
Purple Color—Red 40, Blue 1
Teal Green Color—Green 5
Yellow Color—Yellow 5

The present invention will be illustrated in more detail by the following examples without limiting the scope of the claimed process and formulations in any way.

EXAMPLE 1

Composition useful for improving skin green color foot powder was made according to the following formulation:

Formula 1
about 20% to about 60% by volume magnesium sulfate. about 0 to about 40% by volume vitamin A, and vitamin E, about 40% to about 80% by volume biodegradable surfactants, about 0% to about 20% by volume *melaleuca alternifolia*, about 20% to about 80% by volume sodium carbonate, about 0% to about 20% by volume water, fragrance, about 0.1% propylparaben, about 0 to about 40% propylene glycol, and colors Yellow 5, and Blue I.

EXAMPLE 2

Composition useful for improving skin purple color foot powder was made according to the following formulation:

Formula 2
about 20% to about 60% by volume magnesium sulfate. about 0 to about 40% by volume vitamin A, and vitamin E, about 40% to about 80% by volume biodegradable surfactants, about 0% to about 20% by volume *melaleuca alternifolia*, about 20% to about 80% by volume sodium carbonate, about 0% to about 20% by volume water, fragrance, about 0.1% propylparaben, about 0 to about 40% propylene glycol, and colors Red 40, and Blue 1.

In conclusion, therefore, it is made known that the present invention and the embodiments disclosed are able to carry out the objectives set forth. The description is intended to cover all aspects of the invention in the best possible way for understanding.

It will be understood that the above description of the present invention is susceptible to various modifications, changes and adaptations, and the same are intended to be comprehended within the meaning and range of equivalents of the appended claims.

The invention claimed is:

1. A composition useful for improving rough or hard skin on the feet comprising: 20-60% magnesium sulfate, vitamins A and E, *melaleuca alternifolia,* 40-80% of biodegradable surfactants, 20-80% sodium carbonate, water, fragrance, 0.1% of propylparaben, propylene glycol, optionally containing one or more FD&C colors, and is prepared by thoroughly blending all ingredients.

2. Composition useful for improving rough or hard skin on the feet according to claim 1 wherein about 0% to about 40% by volume are present vitamin A and vitamin E.

3. Composition useful for improving rough or hard skin on the feet according to claim 1 wherein *melaleuca alternifolia* is about 0% to about 20% by volume.

4. Composition useful for improving rough or hard skin on the feet according to claim 1 wherein water is about 0% to about 20% by volume.

5. Composition useful for improving rough or hard skin on the feet according to claim 1 wherein fragrance is about 0% to about 20% by volume.

6. Composition useful for improving rough or hard skin on the feet according to claim 1 wherein propylene glycol is about 0% to about 40% by volume.

7. Composition useful for improving rough or hard skin on the feet according to claim 1, wherein the FD&C colors are selected from the group consisting of FD&C colors yellow 5, red 40, red 3, blue 1, red 33, or combinations thereof.

\* \* \* \* \*